(12) United States Patent
Oliver et al.

(10) Patent No.: US 8,906,053 B2
(45) Date of Patent: Dec. 9, 2014

(54) SYSTEMS AND METHODS FOR SURGICAL REMOVAL OF BRAIN TUMORS

(75) Inventors: Dana A. Oliver, Jacksonville, FL (US); Louis M. Shadeck, Jacksonville, FL (US); Roy Galvin, Southlake, TX (US); Robert Spetzler, Phoenix, AZ (US)

(73) Assignee: Medtronic Xomed, Inc., Jacksonville, FL (US)

( * ) Notice: Subject to any disclaimer, the term of this patent is extended or adjusted under 35 U.S.C. 154(b) by 842 days.

(21) Appl. No.: 11/938,625

(22) Filed: Nov. 12, 2007

(65) Prior Publication Data

US 2009/0124975 A1 May 14, 2009

(51) Int. Cl.
*A61B 17/32* (2006.01)
*A61M 31/00* (2006.01)
*A61B 17/02* (2006.01)
*A61B 19/00* (2006.01)
*A61M 1/00* (2006.01)

(52) U.S. Cl.
CPC ............ *A61B 17/32002* (2013.01); *A61B 17/02* (2013.01); *A61B 2217/007* (2013.01); *A61B 2019/4889* (2013.01); *A61B 2217/005* (2013.01); *A61M 1/0047* (2013.01); *A61B 2017/320044* (2013.01)
USPC .......................................... 606/171; 604/506

(58) Field of Classification Search
CPC ............. A61B 17/02; A61B 17/32002; A61B 2017/320044; A61B 2217/005; A61B 2217/007; A61M 1/0047
USPC .................... 604/22, 164.01, 164.02, 164.09, 604/164.11, 264, 272; 606/167, 169–171, 606/180
See application file for complete search history.

(56) References Cited

U.S. PATENT DOCUMENTS

| 3,055,370 A | * | 9/1962 | McKinney et al. ............ 606/129 |
| 4,517,977 A | | 5/1985 | Frost |
| 5,268,785 A | | 12/1993 | Crenshaw et al. |
| 5,403,276 A | | 4/1995 | Schechter et al. |
| 5,403,307 A | | 4/1995 | Zelman |

(Continued)

FOREIGN PATENT DOCUMENTS

| DE | 20117907 U1 | 1/2002 |
| EP | 1029509 A1 | 8/2000 |
| WO | 0224084 A1 | 3/2002 |

OTHER PUBLICATIONS

PCT Search Report mailed Jun. 6, 2009 for Int'l Application No. PCT/US2008/082958 (20 pgs.).

*Primary Examiner* — Nathan R Price
(74) *Attorney, Agent, or Firm* — Dicke, Billig & Czaja, PLLC

(57) ABSTRACT

A method for treating a brain tumor includes providing a surgical instrument having an inner member and an outer member. The outer member has a distal region forming a cutting window and an optional distal elevator tip. The inner member is rotatably received within the outer member, and has a cutting tip that is exposed at the window. The cutting tip and the distal region of the outer member combine to define a cutting implement. An opening is created through the patient's skull to provide access to a brain tumor target site. The cutting implement is delivered through the opening to the target site. The elevator tip is inserted partially between the tumor and tissue of the target site, and the cutting tip is placed into contact with the tumor and operated to cut the tumor. The target site is selectively aspirated to remove cut tumor tissue.

18 Claims, 12 Drawing Sheets

(56) References Cited

U.S. PATENT DOCUMENTS

| | | |
|---|---|---|
| 5,492,527 A * | 2/1996 | Glowa et al. .............. 604/22 |
| 5,643,304 A | 7/1997 | Schechter et al. |
| 5,669,876 A | 9/1997 | Schechter et al. |
| 5,685,840 A | 11/1997 | Schechter et al. |
| 5,694,951 A | 12/1997 | Bonutti |
| 5,709,698 A | 1/1998 | Adams et al. |
| 5,718,709 A * | 2/1998 | Considine et al. ......... 606/115 |
| 5,722,985 A | 3/1998 | Pettus |
| 5,849,023 A | 12/1998 | Mericle |
| 5,935,131 A | 8/1999 | Bonutti |
| 6,024,751 A | 2/2000 | Lovato et al. |
| 6,156,049 A | 12/2000 | Lovato et al. |
| 6,174,313 B1 | 1/2001 | Bonutti |
| 6,312,441 B1 | 11/2001 | Deng |
| 6,428,498 B2 | 8/2002 | Uflacker |
| 6,436,067 B1 | 8/2002 | Deng et al. |
| 6,468,289 B1 | 10/2002 | Bonutti |
| 6,503,263 B2 | 1/2003 | Adams |
| 6,543,455 B2 | 4/2003 | Bonutti |
| 6,607,534 B2 | 8/2003 | Bonutti |
| 6,652,532 B2 | 11/2003 | Bonutti |
| 6,835,198 B2 | 12/2004 | Bonutti |
| 2002/0020555 A1 | 2/2002 | Daido |
| 2002/0045903 A1 | 4/2002 | Bonutti |
| 2002/0055755 A1 | 5/2002 | Bonutti |
| 2002/0082631 A1 | 6/2002 | Bonutti |
| 2002/0091403 A1 | 7/2002 | Bonutti |
| 2002/0099410 A1 | 7/2002 | Ben David |
| 2003/0009172 A1 | 1/2003 | Bonutti |
| 2003/0107814 A1 | 6/2003 | Altmann |
| 2003/0135151 A1 | 7/2003 | Deng |
| 2003/0181934 A1 | 9/2003 | Johnston et al. |
| 2004/0092992 A1 | 5/2004 | Adams et al. |
| 2005/0054972 A1 | 3/2005 | Adams et al. |
| 2005/0107814 A1 | 5/2005 | Johnston et al. |
| 2005/0131436 A1 | 6/2005 | Johnston et al. |
| 2005/0131437 A1 | 6/2005 | Johnston et al. |
| 2005/0165435 A1 | 7/2005 | Johnston et al. |
| 2005/0187572 A1 | 8/2005 | Johnston et al. |
| 2005/0267501 A2 | 12/2005 | Johnston et al. |

* cited by examiner

SYSTEMS AND METHODS FOR SURGICAL REMOVAL OF BRAIN TUMORS

BACKGROUND

The present disclosure relates to treatment of brain tumors. More particularly, it relates to surgical systems, instruments, and methods useful in reducing and/or removing brain tumors.

Brain surgery is the treatment of choice for accessible brain tumors. The goal of surgery is to remove as much tumor tissue as possible. The most commonly performed surgery for removal of a brain tumor is a craniotomy. In general, the neurosurgeon makes an incision into the scalp, cranium, dura, meninges, and cortex to expose an area of brain over the tumor. Location and removal of the tumor then takes place. In this regard, a variety of surgical instruments, such as a cavitational ultrasonic surgical aspirator (CUSA) or a surgical laser knife, are commonly used.

The delicate tissues associated with the human brain anatomy give rise to several concerns when using a CUSA, laser knife, or other brain surgery instrument. By way of reference, the brain is covered by three membranes or meninges that in turn are surrounded by the skull. The three layers of meninges are the dura mater (immediately beneath the skull), the arachnoid, and the pia mater. Spinal fluid flows in the space between the arachnoid and the pia mater membranes, known as the subarachnoid space. These meninges are thin and delicate, with the pia mater carrying or maintaining the many blood vessels associated with the brain. Due to the friable nature of especially the pia mater, neurosurgeons must exercise great care when attempting to surgically remove a brain tumor; unintended damage to the pia mater can diminish the primary blood supply to the brain. Unnecessary injury to other healthy structures, such as the arachnoid or brain tissue (e.g., cerebral cortex) can also lead to patient impairment. With this in mind, CUSA instruments deliver ultrasonic action to remove tissue and bone. The surgeon attempts to place the ultrasonic cutting tip against tissue to be destroyed. However, high frequency cutting may also occur and damage tissue surrounding the targeted tumor when touched by the instrument's shaft. Further, due to the relatively large size of the CUSA handpiece, it may be difficult to visually confirm placement of the ultrasonic shaft/tip. Similarly, use of a laser knife may give rise to unintended tissue damage due to local heat in and around the incision line.

In light of the above, a need exists for surgical systems and methods for reducing or removing brain tumors while minimizing likelihood of normal tissue damage.

SUMMARY

Some aspects in accordance with principles of the present disclosure relate to a surgical method for surgically treating a brain tumor of a patient. The method includes providing a surgical system including a surgical instrument having an inner member and an outer member. The inner member includes a distal cutting tip, whereas the outer member has a distal region forming a cutting window and elevator tip distal the cutting window. In this regard, the inner member is rotatably received within the outer member such that the cutting tip is exteriorly exposed at the cutting window. Further, the cutting tip and the distal region of the outer member combine to define a cutting implement. With this in mind, an opening is created through a skull of the patient to provide external access to a target site at which the brain tumor is located. The cutting implement is delivered through the opening to the target site. The elevator tip is inserted partially between the tumor and tissue of the target site, such as one or more of dura, arachnoid, pia, and cerebral cortex. The cutting tip is placed into contact with the tumor. The inner member is then moved relative to the outer member, thereby causing the cutting tip to cut tissue of the tumor. Finally, the target site is selectively aspirated to remove the cut or debrided tumor tissue. By using the elevator tip to at least partially isolate the tumor and selectively aspirating the target site, the likelihood of damaging normal tissue is minimized. In some alternative aspects, methods of the present disclosure further include varying a level of vacuum (or aspiration rate) at the target site throughout the procedure, with the tumor being drawn into contact with the cutting tip via applied aspiration prior to a cutting operation.

Other aspects in accordance with the present disclosure relate to a surgical system for debriding a brain tumor. The system includes a surgical cutting instrument, a motor, and a source of negative pressure. The cutting instrument includes an inner member, an outer member, a handpiece, and an aspiration control device. The inner member includes a distal cutting tip, whereas the outer member has a distal region forming a cutting window and an elevator tip distal the cutting window. The handpiece maintains the inner and outer members such that the inner member is rotatably received within the outer member, with the cutting tip being exteriorly exposed at the cutting window. Further, the cutting tip and the distal region combine to define a cutting implement. The aspiration control device is maintained by the handpiece. The motor is connected to the inner member for moving the inner member relative to the outer member, for example as part of a cutting operation. Finally, the source of negative pressure is fluidly connected to the cutting implement via a fluid pathway. With this in mind, the aspiration control device is fluidly connected to the fluid pathway for providing user control over a level of vacuum applied at the cutting implement. The above system is highly useful in performing brain tumor surgery, affording the neurosurgeon the ability to more precisely effectuate cutting only of the brain tumor, as well as to control aspiration applied to the target site. With some alternative constructions in accordance with principles of the present disclosure, the surgical instrument further includes a control assembly configured to allow selective rotation of the outer member relative to the inner member. In yet other alternative constructions, the elevator tip has a scoop-like or curette shape.

Yet other aspects in accordance with the present disclosure relate to a surgical system for debriding a brain tumor, including a surgical cutting instrument, a motor, and a source of negative pressure. The cutting instrument includes an inner member, an outer member, a handpiece, and an aspiration control device. The inner member includes a distal cutting tip, whereas the outer member has a distal region forming a cutting window. The handpiece maintains the inner and outer members such that the inner member is rotatably received within the outer member, the cutting tip being exteriorly exposed at the cutting window. Further, the cutting tip and the distal region combine to define a cutting implement. The aspiration control device is maintained by the handpiece. The motor is connected to the inner member for moving the inner member relative to the outer member, for example as part of a cutting operation. Finally, the source of negative pressure is fluidly connected to the cutting implement via a fluid pathway. With this in mind, the aspiration control device is fluidly connected to the fluid pathway and forms a user interface opening that is open to ambient. With this construction, the user interface opening is adapted to provide user control over a level of vacuum applied at the cutting implement. For example, by obstructing more or less of the interface opening, the level of vacuum applied at the cutting implement is increased or decreased, respectively. With some alternative constructions in accordance with principles of the present disclosure, the system is configured such that when the source of negative pressure is generating negative pressure and the user interface hole is exteriorly unobstructed, a level of vacuum applied at the cutting implement is substantially zero.

DETAILED DESCRIPTION

Figure 1:
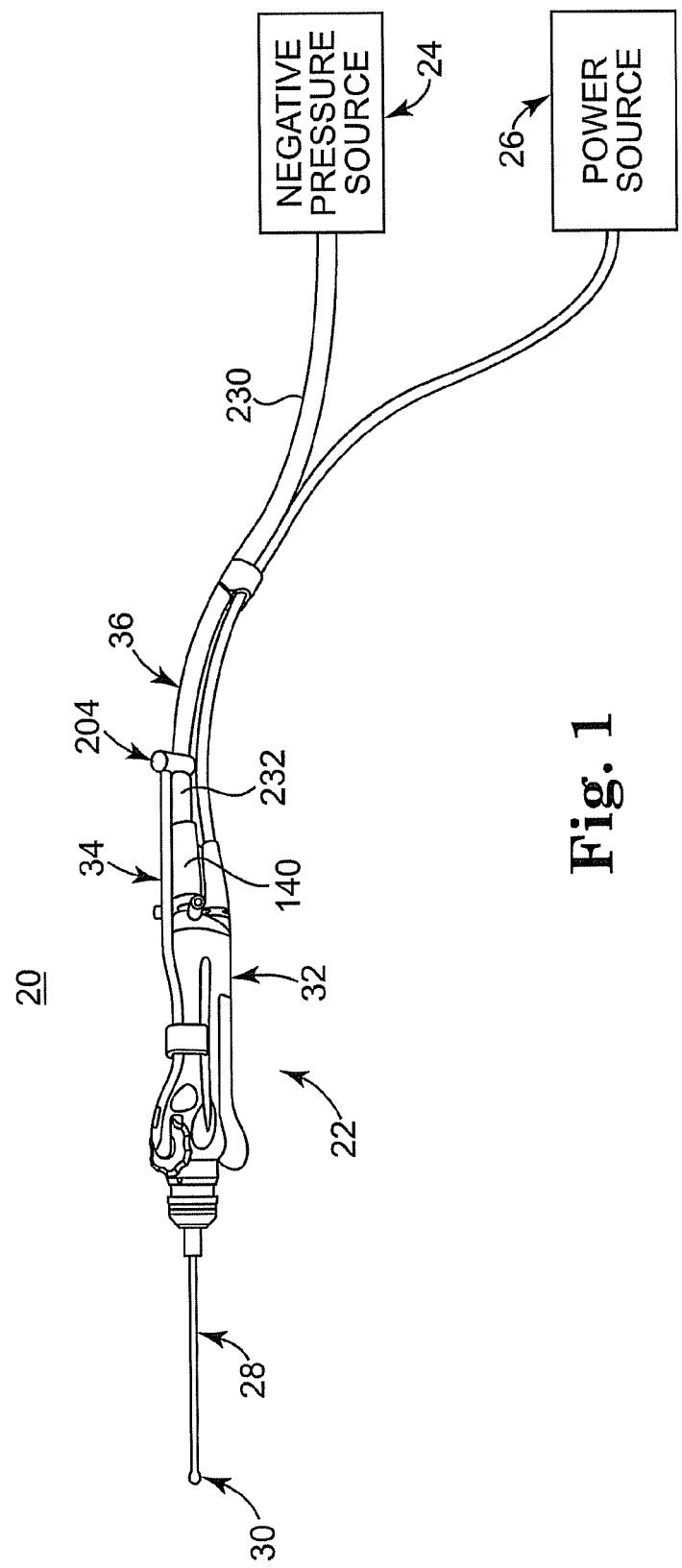
FIG. 1 is a schematic illustration of a system for surgically reducing or removing a brain tumor in accordance with principles of the present disclosure.

A surgical system 20 in accordance with aspects of the present disclosure for use in debriding a brain tumor as part of brain surgery is shown in FIG. 1. The system 20 includes a surgical cutting instrument 22, a source of negative pressure 24, and a power source 26. Details on the various components are provided below. In general terms, however, the surgical instrument 22 includes a blade assembly 28 forming a cutting implement 30 (referenced generally), a handpiece 32, and an aspiration control device 34. The source of negative pressure 24 is fluidly connected to the cutting implement 30 via a fluid pathway 36 extending through the handpiece 32. The aspiration control device 34 is also fluidly connected to the fluid pathway 36. Finally, the power source 26 is electrically connected to a motor (not shown) maintained by the handpiece 32. During use in surgically reducing or removing a brain tumor, the cutting implement 30 is deployed to a target site, with the user manipulating the handpiece 32 to achieve a desired position of the cutting implement 30 relative to the brain tumor. The power source 26 energizes the motor to effectuate a tumor cutting operation at the cutting implement 30. Finally, the aspiration control device 34 is manually operated by the user to selectively effectuate aspiration at the cutting implement 30 via a vacuum generated by the source of negative pressure 24. In some configurations, the aspiration control device 34 affords the user the ability to vary the rate or level of aspiration, as well as an aggressiveness of cutting at the cutting implement 30.

Figure 2:
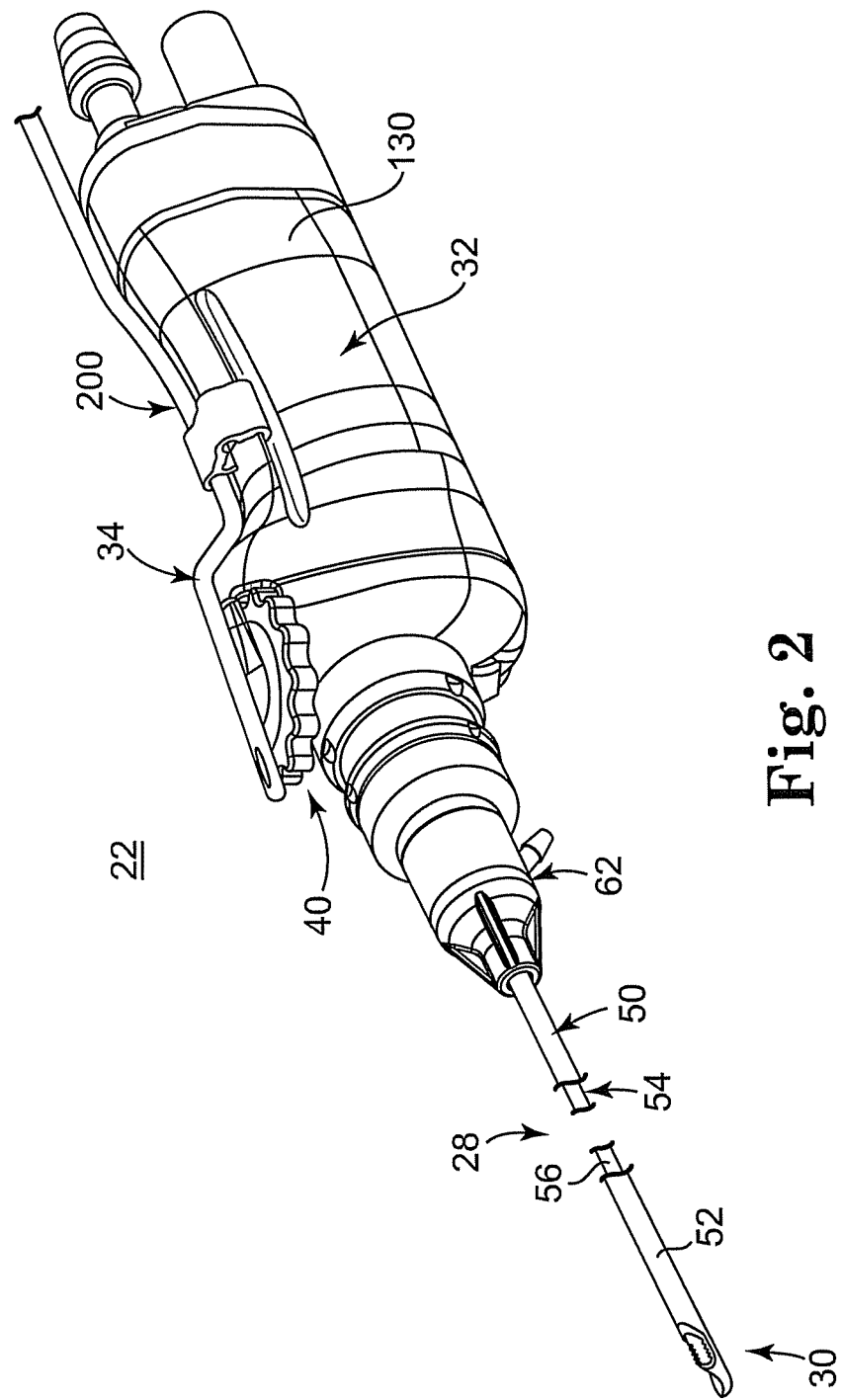
FIG. 2 is a perspective view of a surgical instrument useful with the system of FIG. 1.

With the above general construction of the system 20 in mind, features associated with the surgical instrument 22 in accordance with aspects of the present disclosure are shown in greater detail in FIG. 2. The surgical instrument 22 includes the blade assembly 28, the handpiece 32, and the aspiration control device 34 as mentioned above. In addition, in some embodiments, the surgical instrument 22 includes an optional control assembly 40 (referenced generally) configured to provide user control over a rotational position of a component of the blade assembly 28 as described below.

The blade assembly 28 can assume a variety of forms, and in some configurations includes an outer member assembly 50 having an outer member 52, and an inner member assembly 54 having an inner member 56. In general terms, the inner member 56 is rotatably disposed within the outer member 52, with other components of the assemblies 50, 54 effectuating connection to the handpiece 32. Regardless, the outer and inner members 52, 56 extend distally from the handpiece 32, and combine to form the cutting implement 30 as described below. As a point of reference, while the blade assembly 28 is shown as including two of the members 52, 56, in other configurations, three or more co-axially assembled members can be provided. Further, the blade assembly 28, and in particular the members 52, 56, can have a linear or straight configuration as shown, or can alternately have a curved construction (such as by the inclusion of a curved member encompassing at least a portion of the outer member 52).

Figure 3:
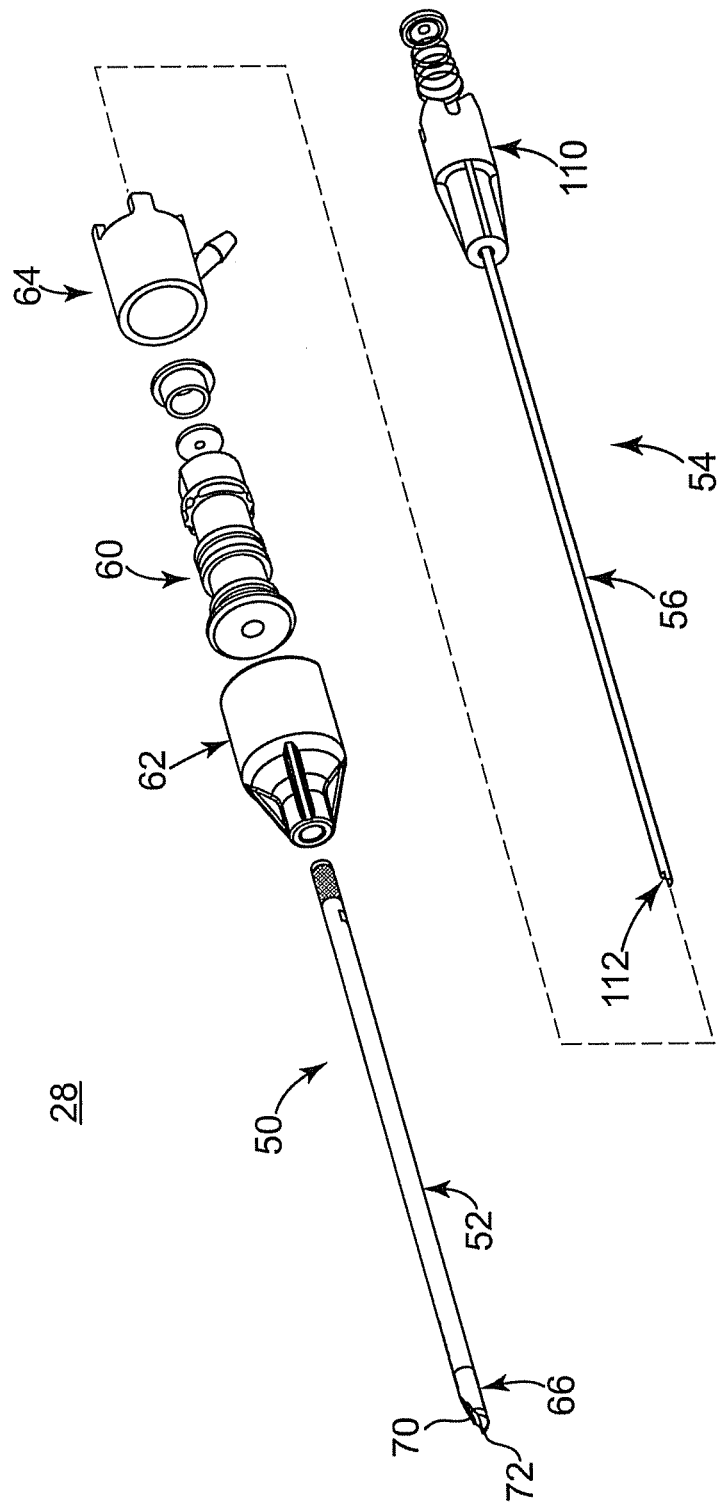
FIG. 3 is an exploded view of a blade assembly portion of the instrument of FIG. 2.

With further reference to FIG. 3, with some configurations, in addition to the outer member 52, the outer member assembly 50 includes an outer member hub 60, a collet 62, and an optional irrigation hub 64. The outer member 52 is secured to the outer member hub 60, with the collet 62 facilitating attachment to the handpiece 32. Further, where provided, the irrigation hub 64 facilitates delivery of an irrigation fluid to the outer member 52. Other constructions appropriate for assembling the outer member 52 to the handpiece 32 are also acceptable. Regardless, the outer member 52 is tubular in some embodiments, and forms a distal region 66. The distal region 66, in turn, forms in some configurations a cutting window 70 and an elevator tip 72 distal the cutting window 70.

Figure 4A:
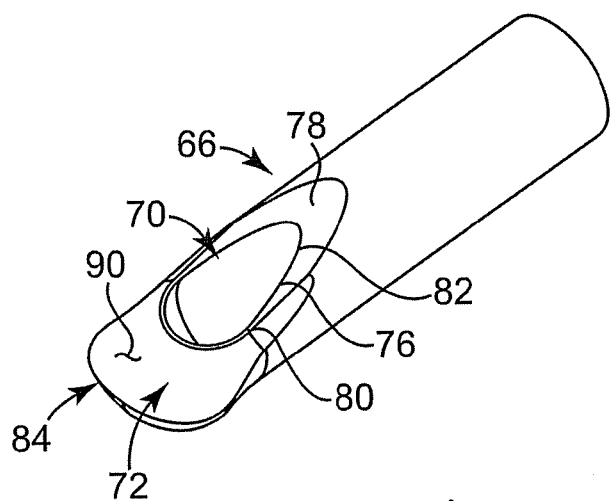
FIG. 4A is an enlarged, perspective view of a distal region of an outer tubular member of the assembly of FIG. 3.
Figure 4B:
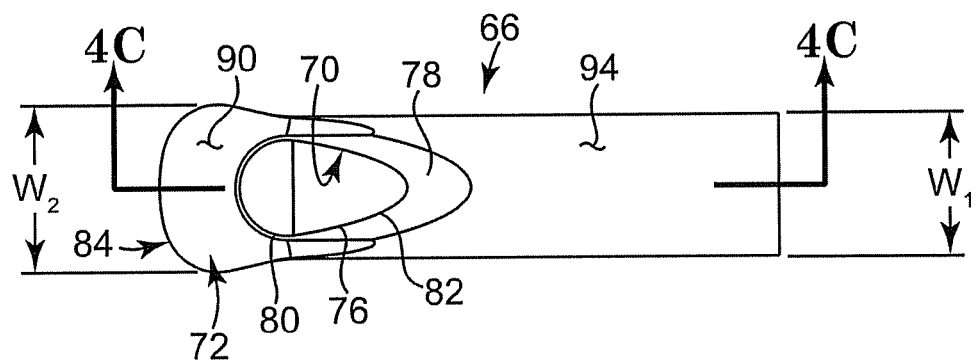
FIG. 4B is a top view of the distal region of FIG. 4A.
Figure 4C:
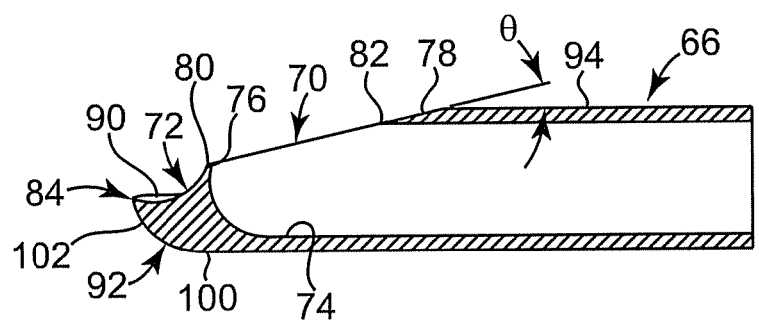
FIG. 4C is a cross-sectional view of the distal region of FIG. 4B along the line 4C-4C.

The distal region 66 can be an integrally formed component of the outer member 52, or can be separately formed and assembled to other components (e.g., the distal region 66 can be formed and then attached to an appropriately sized, rigid metal tube in completing the outer member 52). Regardless, one construction of the distal region 66 in accordance with principles of the present disclosure is shown in greater detail in FIGS. 4A-4C. As best shown in FIG. 4C, the distal region 66 forms a lumen 74 that is otherwise open at the cutting window 70 (and continues proximally through at least a substantial portion of a remainder of the outer member 52 (FIG. 3)). With this mind, the cutting window 70 is defined by a cutting window wall 76. A recessed portion 78 is formed in the distal region 66 about at least a proximal portion of the cutting window wall 76, such that the distal region 66 tapers in wall thickness along the recessed portion 78. As best shown in FIGS. 4A and 4B, the cutting window 70 can have a tear drop-like shape in longitudinal length, decreasing in lateral perimeter width from a distal segment 80 to a proximal segment 82.

The elevator tip 72 extends distal the cutting window 70, terminating at a sharpened or blade edge 84. In this regard, the elevator tip 72 is closed relative to the lumen 74 and is defined by opposing, first and second surfaces 90, 92. As a point of reference, and relative to the orientation of FIG. 4C, the first surface 90 can be designated as an upper surface, and is contiguous with a surface 94 of the distal region 66 at which the cutting window 70 is otherwise defined. Conversely, the second surface 92 serves as a bottom surface. Regardless, the first surface 90 has a scoop-like shape, defining a concave curvature in extension from the cutting window 70 to the blade edge 84. The second surface 92 is generally defined by a proximal portion 100 and a distal portion 102. As best shown in FIG. 4C, the proximal portion 100 extends in a linear fashion (in longitudinal cross-section) relative to the cutting window 70. The distal portion 102, however, has a convex curvature in extension from the proximal portion 100 to the blade edge 84. In some embodiments, a continuous curvature is defined by the first surface 90 and the distal portion 102 of the second surface 92, with the continuously curved surfaces meeting at the blade edge 84. In addition to being sharp, the blade edge 84 is located at or below an angled cut defined by the cutting window wall 76. That is to say, FIG. 4C reflects that in longitudinal cross-section, the cutting window wall 76/recessed portion 78 forms an angle θ relative to the surface 94, with the cutting window wall 76 tapering in height along the angle θ from the proximal segment 82 to the distal segment 80. Relative to the orientation of FIG. 4C, the blade edge 84 intersects or is "below" an imaginary line defined by the angle θ. It has been surprisingly found that the resultant configuration is well-suited for surgical brain tumor removal procedures. Alternatively, however, other constructions may alternatively be employed.

In addition to the curvatures described above, distal extension of the elevator tip 72 from the cutting window 70 is characterized by the distal region 66 exhibiting an increase in transverse width. More particularly, and as best shown in FIG. 4B, the distal region 66 (as well as at least a majority of the outer member 52 (FIG. 3) proximal the distal region 66) has a transverse width (or diameter) $W_1$ immediately proximal, and along at least a substantial portion of, the cutting window 70. The elevator tip 72 expands in a generally radially outward fashion in distal extension from the cutting window 70, defining a maximum transverse width (or diameter) $W_2$. As shown, the maximum width $W_2$ of the elevator tip 72 is greater than the width $W_1$ of the distal region 66 proximal the cutting window 70.

The above construction of the elevator tip 72 (e.g., curved surfaces, increased width, and the blade edge 84) combine to provide the elevator tip 72 with a curette-like form. As described below, the elevator tip 72 is highly amenable for interfacing with the delicate tissues encountered during brain surgery. The blade edge 84 promotes partial separation or isolation of tumor from brain and other normal tissue, with the curved surfaces 90, 92 assisting in isolating or separating the tumor from other tissue. In other configurations in accordance with the present disclosure, however, the elevator tip 72 can be eliminated. For example, the distal region 66 can terminate at the cutting window 70 that is otherwise axially and radially open to the lumen 74. Alternatively, the cutting window 70 can be formed in the distal region 66 as a side (or radial) window, with the outer member 52 having a relatively uniform outer diameter distal the cutting window 70.

Figure 5:
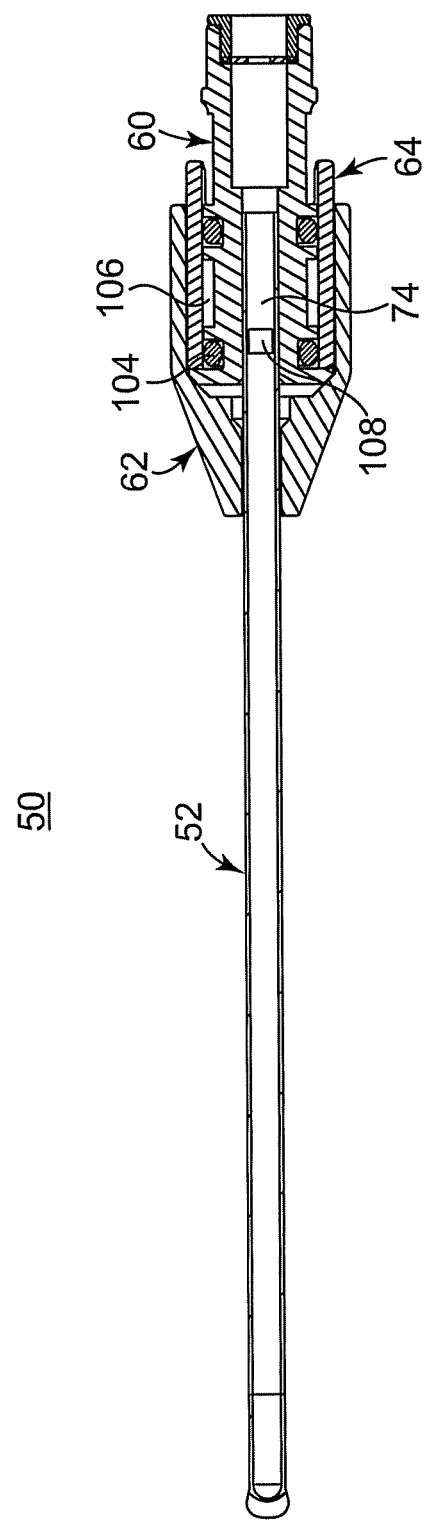
FIG. 5 is a cross-sectional view of the outer member assembly of FIG. 3 upon final construction.

Final construction of the outer member assembly 50 is shown in FIG. 5. The outer member 52 is assembled to the outer member hub 60 that in turn is received within the irrigation hub 64. In this regard, seals 104 (e.g., O-rings) can be provided to effectuate a fluid-tight seal between the irrigation hub 64 and the outer member hub 60. With this construction, then, an irrigation liquid (not shown) can be delivered to the lumen 74 of the outer member 52 via a sealed gap 106 between the hubs 60, 64 and a bore 108 formed in the outer member 52. The assembled hubs 60, 64 are coaxially received with the collet 62, with the outer member 52 extending distal the collet 62 as shown. Other constructions capable of effectuating flow of irrigation liquid to the outer member 52 are also envisioned; in yet other configurations, the irrigation hub 64 (as well as any other irrigation component) can be eliminated.

Figure 6:
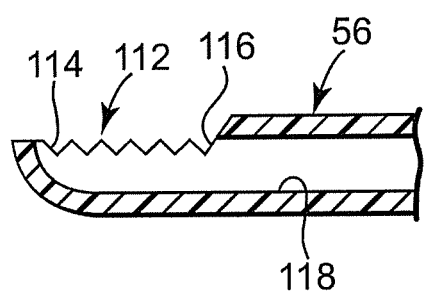
FIG. 6 is an enlarged, cross-sectional view of a portion of an inner member portion of the blade assembly of FIG. 3.

Returning to FIG. 3, the inner member assembly 54 includes the inner member 56, as well as an inner member hub 110. As described below, the inner member hub 110 maintains the inner member 56, and facilitates connection of the inner member assembly 54 to a motor (not shown). Thus, the inner member hub 110 can assume a variety of forms. Regardless, with some constructions, the inner member 56 is tubular, forming a distal cutting tip 112. For example, and as shown in FIG. 6, the cutting tip 112 can include a series of serrations or teeth 114. With this but one acceptable configuration, the teeth 114 are formed about an aperture 116 that is otherwise open to a lumen 118 defined by the inner member 56. As described below, the aperture 116 and the lumen 118 serve as an aspiration outlet of the aspiration fluid pathway 36 (FIG. 1) otherwise employed for aspirating a target site. Alternatively, the cutting tip 112 can assume other forms that may or may not include an aperture fluidly connected to a lumen. For example, the cutting tip 112 can be a closed burr.

Figure 7:
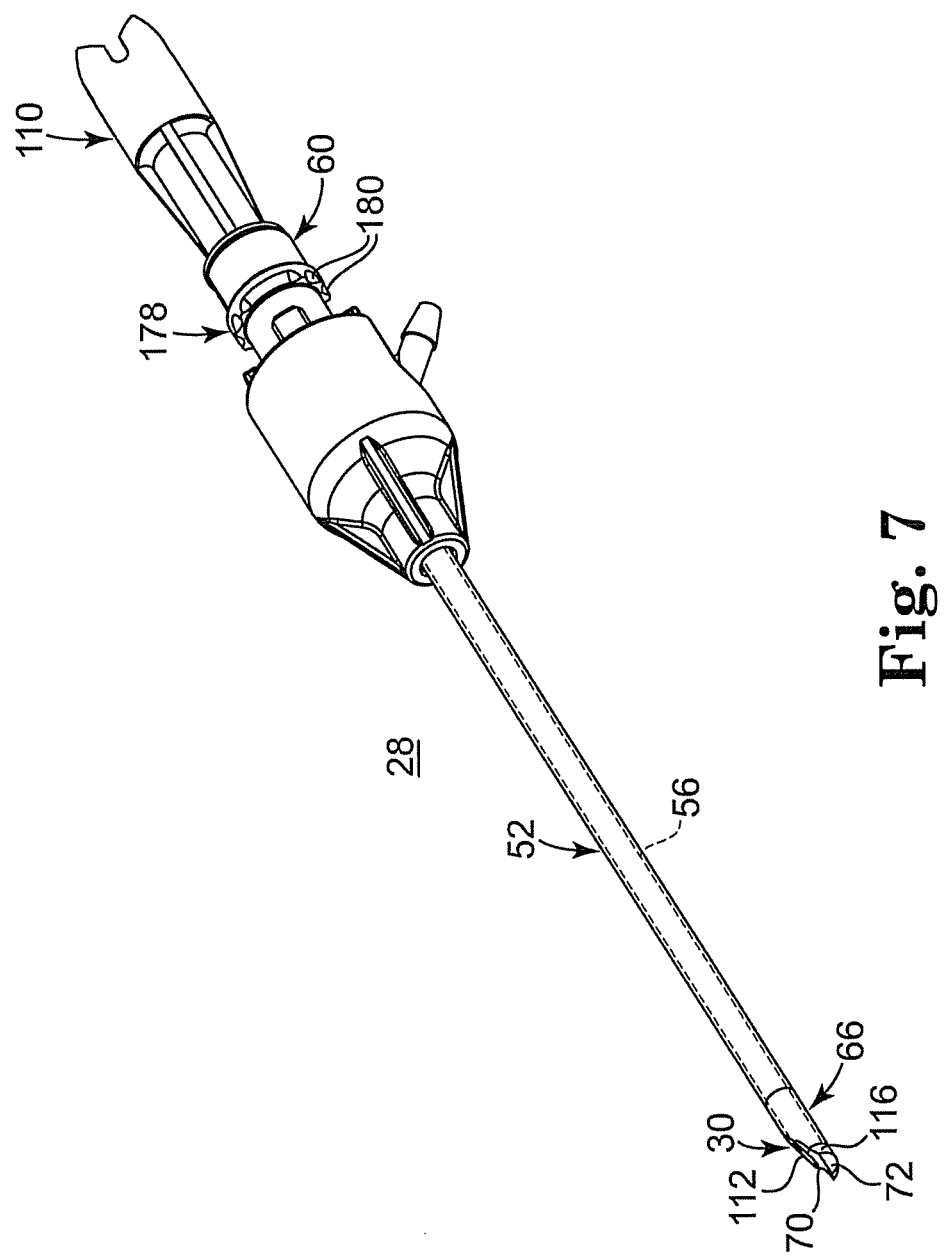
FIG. 7 is a perspective view of the blade assembly of FIG. 3 upon final assembly.

Final construction of the blade assembly 28 is shown in FIG. 7. As a point of reference, while the outer and inner members 52, 56 have been shown in as being linear, in other configurations, one or more bends or curves can be formed and/or additional tubular member(s) provided. The inner member 56 is received within the lumen 74 (FIG. 4C) of the outer member 52, and is attached to the inner member hub 110. The inner member hub 110, in turn, is positioned proximal the outer member hub 60 and is rotatable relative thereto, such that rotation of the inner member hub 110 effectuates rotation of the inner member 56 relative to the outer member 52. Further, the cutting tip 112 of the inner member 56 is positioned at the cutting window 70 of the outer member 52. Thus, the cutting tip 112 is exteriorly exposed via the cutting window 70 for performing a cutting or debriding procedure. Finally, the distal region 66 of the outer member 52 (e.g., the cutting window 70 and the elevator tip 72) combine with the cutting tip 112 to form the cutting implement 30. Aspiration is effectuated at the cutting implement 30 via the aperture 116 provided with the inner member 56 (with the aperture 116 being exteriorly open through the cutting window 70). Alternatively, aspiration or suctioning at the cutting implement 30 can be provided by the outer member 52, a separate tubing carried by the cutting implement 30, etc. Similarly, irrigation is provided at the cutting implement via the outer member 52/cutting window 70, although in other embodiments, an additional irrigation supply tube (carried with or separate from the cutting implement 30) can be provided.

Figure 8:
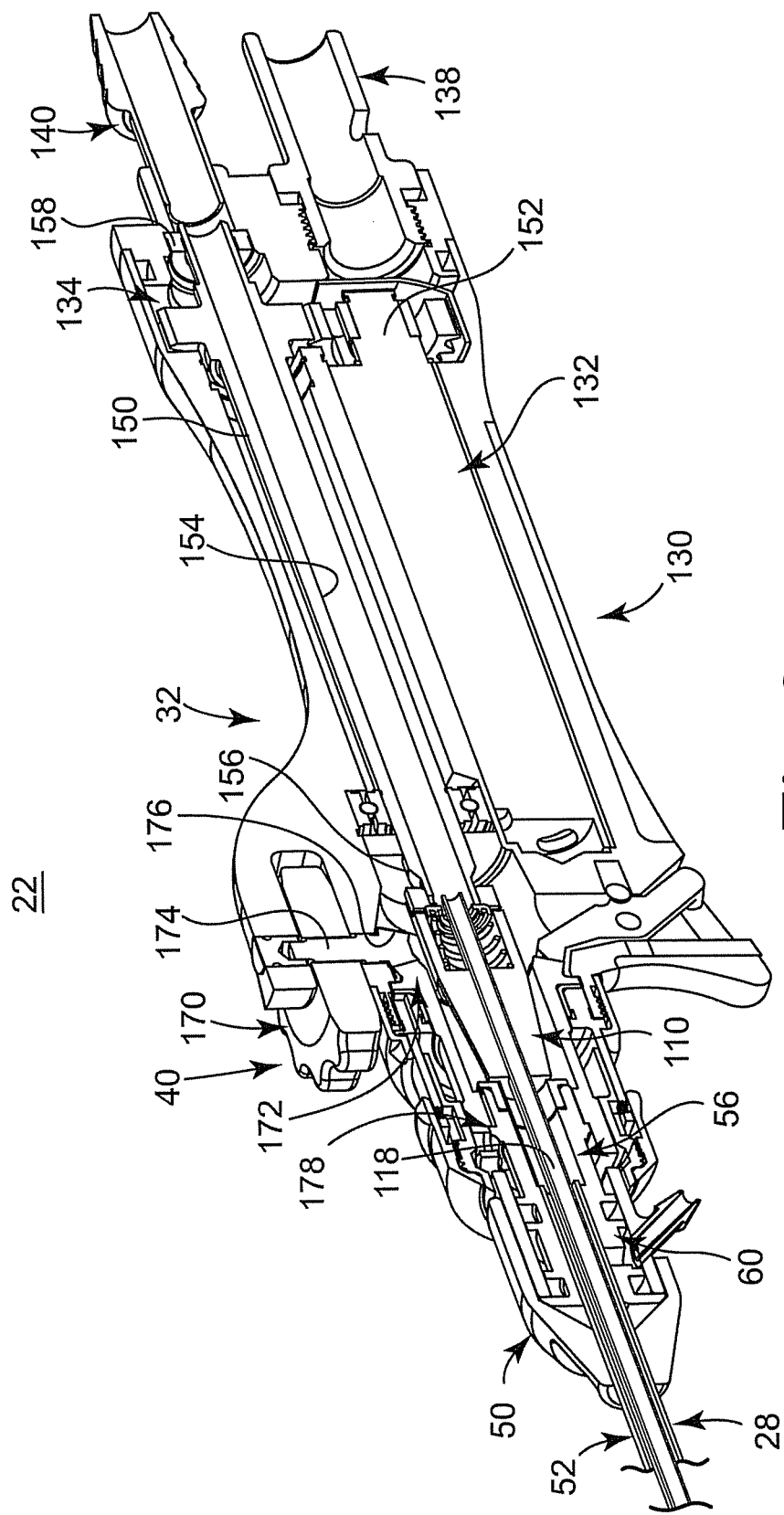
FIG. 8 is a cross-sectional view of a portion of the instrument of FIG. 2.

Returning to FIG. 2, the handpiece 32 can assume a variety of forms that promote manipulation of the blade assembly 28/cutting implement 30 by a user, as well as powered movement of the inner member 56 relative to the outer member 52. For example, FIG. 8 illustrates one construction of the handpiece 32 in accordance with the principles of the present disclosure. As a point of reference, for ease of illustration, the aspiration control device 34 (FIG. 2) is omitted from the view of FIG. 8. Further, the handpiece 32 is shown in FIG. 8 as being assembled to a portion of the blade assembly 28. With this in mind, the handpiece 32 includes a housing 130, the control assembly 40, a motor 132 (shown schematically in FIG. 8), and a drive coupling 134. The motor 132 is secured within the housing 130, with the housing 130 forming a conduit 138 through which wiring (not shown) otherwise providing power to the motor 132 can extend. Further, the housing 130 preferably forms or includes an aspiration port 140 for fluidly connecting the blade assembly 28 to the source of negative pressure 24 (FIG. 1) as described below. The drive coupling 134 mechanically connects the motor 132 to the inner member hub 110, and thus the inner member 56. To this end, a wide variety of constructions can be employed. With some configurations, however, the drive coupling 134 includes an output shaft 150 rotatably linked (e.g., geared) to a drive shaft 152 of the motor 132. The output shaft 150 can assume various forms, and with some constructions forms a passage 154 that, upon final assembly, fluidly connects the aspiration port 140 with a passageway 156 formed by the inner member hub 110 (and thus with the lumen 118 of the inner member 56 otherwise assembled within the passageway 156). Optional dynamic seals 158 can be included to better ensure a fluid-tight seal between the passage 154 and the aspiration port 140.

The optional control assembly 40 facilitates rotation of the outer member 52 relative to the inner member 56 as described below, and can assume a variety of forms. In some constructions, the control assembly 40 includes an actuator 170 and a translation mechanism 172. The actuator 170 can be akin to a wheel, and is rotatably assembled to the housing 130. The translation mechanism 172 is configured to translate rotation of the actuator 170 to the outer member hub 60, and thus the outer member 52. In some embodiments, the translation mechanism 172 includes a post 174 connected to and extending from the actuator 170. In this regard, an end 176 of the post 174 opposite the actuator 170 (or other intermediate body or bodies interconnecting the post end 176 and the outer member hub 60) is adapted to interface with an engagement feature 178 of the outer member hub 60. More particularly, and as best shown in FIG. 7, in some constructions, the engagement feature 178 of the outer member hub 60 is a series of circumferentially disposed indentations 180. Returning to FIG. 8, the post end 176 is configured to interface with the indentations 180, akin to a ball and detent relationship. With this configuration, then, rotation of the actuator 70 is translated by the post 174 to the outer member hub 60. Rotation of the outer member hub 60, in turn, rotates the outer member 52. Because the outer member hub 60 is not otherwise affixed to other components of the inner member assembly 54, rotation of the outer member hub 60 results in rotation of the outer member 52 relative to the inner member 56. Importantly, rotation of the outer member 52 can be achieved by a user without overt movement of the housing 130. The user, while grasping the housing 130 in his or her hand, the surgeon simply rotates the actuator 170 with a finger (or thumb) of the same hand that is otherwise holding the housing 130.

Figure 9A:
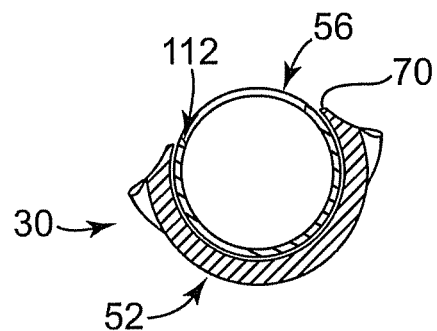
FIGS. 9A and 9B illustrate operation of a cutting implement portion of the instrument of FIG. 8.
Figure 9B:
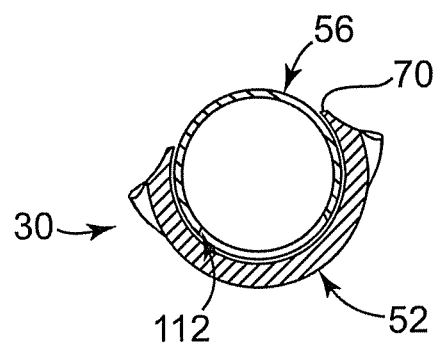

The control assembly 40 can assume a variety of other forms apart from the description provided above, for example as described in U.S. patent application Ser. No. 10/854,020 filed Sep. 22, 2004 and entitled "Surgical Cutting Instrument," the teachings of which are incorporated herein by reference. Conversely, with other constructions of the surgical instrument 22, the control assembly 40 is omitted (i.e., the outer member 52 cannot be independently rotated relative to the inner member 54). Where provided, however, rotation of the outer member 52 relative to the inner member 56 allows the user to selectively shield the cutting tip 112 from unintentionally contacting, and thus possibly damaging, delicate tissue of the brain and surrounding anatomy during a brain tumor debridement procedure. For example, as shown in FIG. 9A (in which only a portion of the outer member 52 is illustrated for purposes of clarity), a rotational position of the outer member 52 relative to the inner member 56 can be selected such that the cutting tip 112 is exteriorly exposed at the cutting window 70. With this orientation, the cutting tip 112 can contact and cut tissue adjacent the cutting implement 30. Conversely, the outer member 52 can be rotated relative to the inner member 56 such that the cutting tip 112 is within the outer member 52, as shown in FIG. 9B. With this arrangement, then, the outer member 52 prevents the cutting tip 112 from contacting, and possibly damaging, tissue. Along these same lines, the outer member 52 can be rotated to position or "face" the cutting window 70 at a desired location (e.g., a brain tumor) without movement of the handpiece 32 (FIG. 8) via the control assembly 40 (FIG. 8). That is to say, once the cutting implement 30 is delivered to a target site, the precise location at which cutting will occur (i.e., the cutting window 70) can be controlled by movement of the actuator 170 (FIG. 8); the surgeon is not required to contort his or her hand(s) to achieve a desired point of cutting/position of the cutting window 70.

Figure 10:
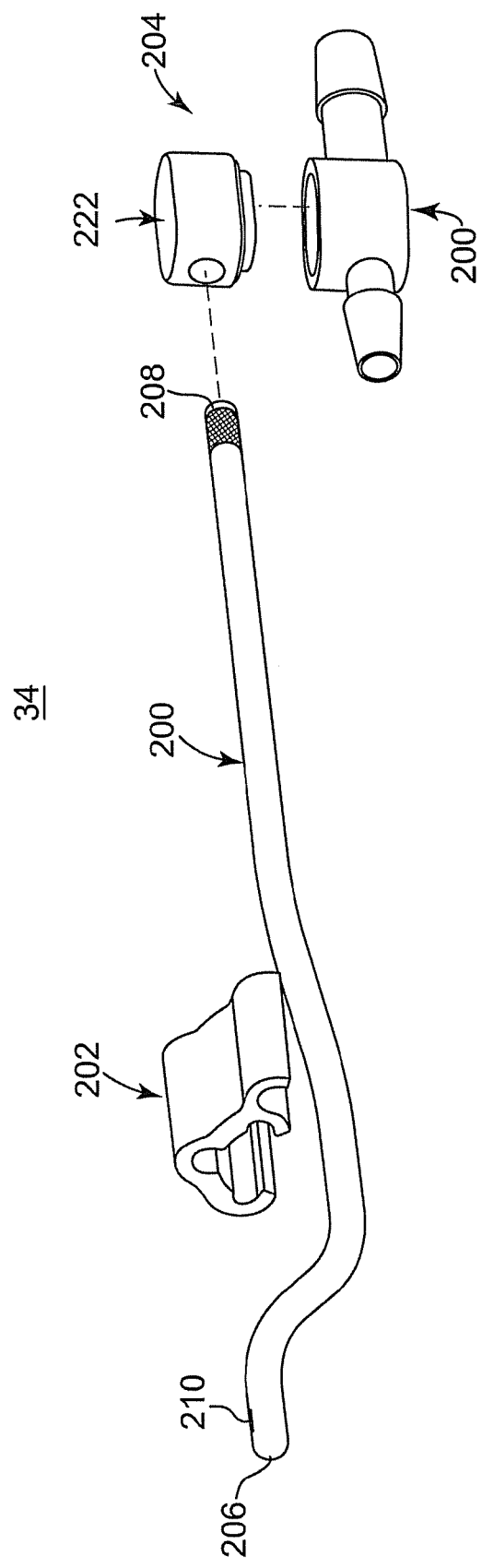
FIG. 10 is an exploded view of an aspiration control device useful with the system of FIG. 1.

Returning to FIG. 2, the aspiration control device 34 can assume a variety of forms, and in some embodiments includes a tube 200 assembled to the housing 130 of the handpiece 32. The tube 200 along with other components of the aspiration control device 34 in accordance with some aspects of the present disclosure is shown in FIG. 10. In addition to the tube 200, the aspiration control device 34 can include a clip 202 and a connector assembly 204. In general terms, the clip 202 connects the tube 200 to the handpiece 32 (FIG. 2). The connector assembly 204 fluidly connects the tube 200 to the fluid pathway 36 (FIG. 1) established with the source of negative pressure 24 (FIG. 1).

Figure 11:
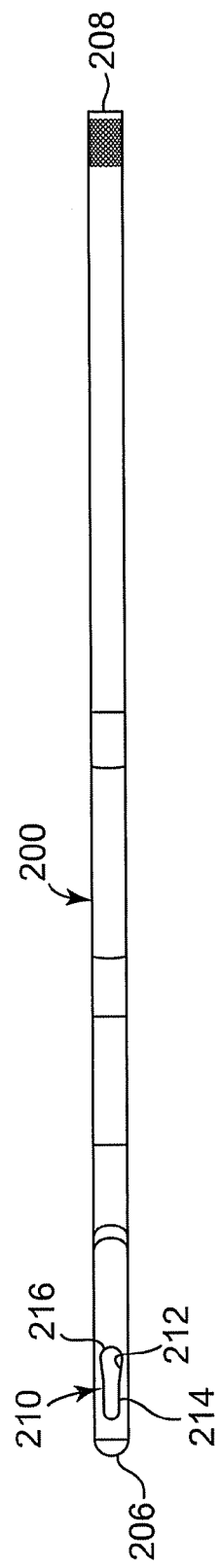
FIG. 11 is a top view of a tube component of the aspiration control device of FIG. 10.

The tube 200 has a shape commensurate with a contour of a surface of the housing 130 (FIG. 2) to which the tube 200 is assembled, and thus may form one or more bends. Regardless, the tube 200 forms a lumen (not shown) extending from a closed, first end 206 to an open, second end 208. Further, the tube 200 forms a user interface hole 210 adjacent the first end 206 that is otherwise fluidly open to the lumen. One construction of the user interface hole 210 is shown in FIG. 11, and is generally sized and shaped to interface with (i.e., be selectively covered by), a user's finger. For example, with some constructions, a perimeter 212 of the user interface hole 210 has a tear drop-like shape, having a relatively linear first segment 214 and an enlarged, rounded second segment 216. This shape generally coincides with a natural shape of an adult's fingertip, although other shapes are also acceptable. As described below, control over the aspiration delivered at the cutting implement 30 (FIG. 1) is selectively effectuated by covering or uncovering the user interface hole 210.

Returning to FIG. 10, the clip 202 can assume a variety of forms adapted to connect the tube 200 to the housing 130 (FIG. 2). In other embodiments, the tube 200 can be permanently affixed to, or formed by (e.g., as an internal bore), the handpiece 32 (FIG. 2), such that the clip 202 can be eliminated.

The connector assembly 204 can also assume a variety of forms, and with some constructions includes a tee connector 220 and a connection block 222. The tee connector 220 is configured for establishing fluid connection with tubing (not shown) between the handpiece 32 (FIG. 1) and the source of negative pressure 24 (FIG. 1). The connection block 222, in turn, is configured for attachment to the second end 208 of the tube 200, as well as to the tee connector 220. Upon final construction, the connector assembly 204 fluidly connects the lumen (not shown) of the tube 200 with the fluid pathway 36 (FIG. 1). A wide variety of other constructions for the connector assembly 204 are equally acceptable.

Returning to FIG. 1, final assembly of the system 20 includes a first tubing 230 extending between, and fluidly connecting, the source of negative pressure 24 and the connector assembly 204. A second tubing 232 fluidly connects the connector assembly 204 with the aspiration port 140 of the handpiece 32. As a result, the fluid pathway 36 is established form the source of negative pressure 24 to the cutting implement 30. More particularly, the source of negative pressure 24 is fluidly connected to the aspiration port 140 via the first tubing 230, the connector assembly 204, and the second tubing 232. The aspiration port 140, in turn, is fluidly connected to the blade assembly 28 via the passage 154 (FIG. 8) of the output shaft 150 (FIG. 8). With some embodiments, the fluid pathway 36 further extends through the lumen 118 (FIG. 6) of the inner member 56 (FIG. 6), and is open at the aperture 116 (FIG. 6). With alternative configurations, the aspiration outlet at the cutting implement 30 can be provided in other forms that may or may not include the aperture 116 of the inner member 56 (e.g., aspiration can be provided via the outer member 52, via a separate tube provided with the blade assembly 28, etc.). Regardless, the tube 200 of the aspiration control device 34 is also in fluid communication with the fluid pathway 36 via the connector assembly 204 with the user interface hole 210 being open to ambient. Thus, the aspiration control device 34 affords the user the ability to control a level of vacuum applied at the cutting implement 30, for example by selectively covering or uncovering the user interface hole 210 (FIG. 11).

A level or rate or vacuum delivered to or experienced at the aperture 116 (FIG. 6), or other aspiration outlet format, will increase as the user interface hole 210 (FIG. 11) is increasingly covered, and vice-versa. With this in mind, the user interface hole 210 has, in some configurations, a larger surface area as compared to the aspiration outlet provided at the cutting implement 30 through which suctioning is otherwise applied. For example, with some constructions, the aspiration outlet provided with the cutting implement 30 is the aperture 116 formed by the inner member 56 (FIG. 3). Commensurate with this description, then, a size of the user interface hole 210 can be selected to be greater than a size of the aperture 116. As a result, when the user interface hole 210 is entirely unobstructed, a vacuum level at the cutting implement 30 (i.e., at the aperture 116) is substantially zero in that the user interface hole 210 provides a path of least resistance for negative pressure within the fluid pathway 36. Further, a user will readily "sense" vacuum or suction at the user interface hole 210, and is thus provided with direct, tactile feedback as to a level of vacuum being applied at the cutting implement 30. Also the user interface hole 210 affords essentially infinite control over the applied vacuum (between zero and maximum generated at the source of negative pressure 24) due to the absence of pre-established indexes or other stop mechanism along the aspiration control device 34.

Figure 12A:
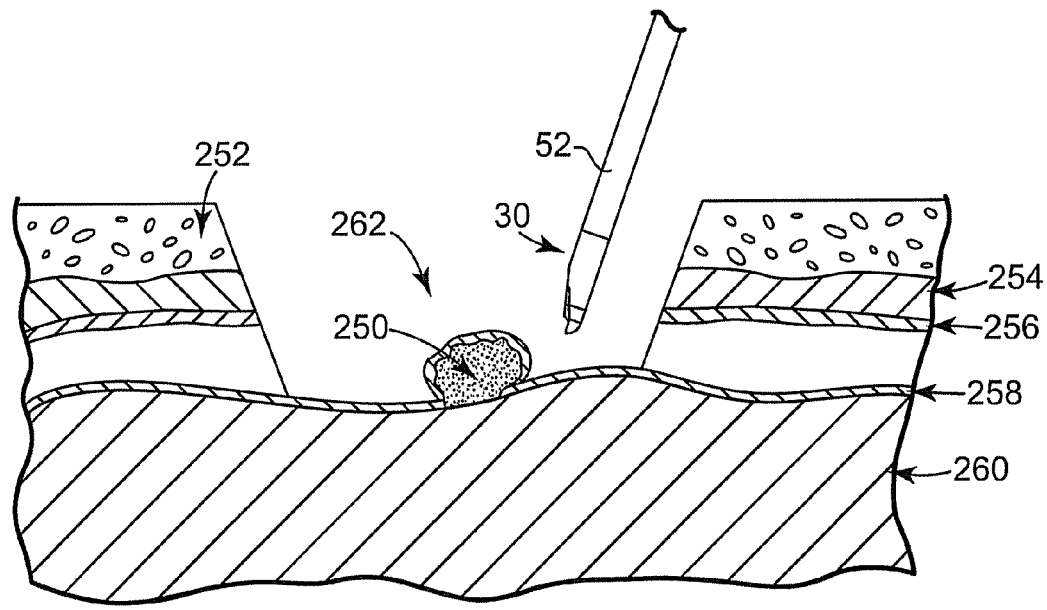
FIGS. 12A and 12B illustrate use of the system of FIG. 1 in surgically removing a brain tumor.

The system 20 is highly useful in the surgical treatment (e.g., removal) of brain tumors (as well as possibly other surgical procedures). In this regard, and with additional reference to FIG. 12A, treatment of a brain tumor 250 in accordance with aspects of the present disclosure includes forming an access opening in the patient's skull 252 (e.g., a conventional craniotomy). As a point of reference, FIG. 12A schematically illustrates other anatomy, including the dura 254, the arachnoid 256, the pia 258, and the cortex 260. The brain tumor 250 is shown as projecting from a natural anatomy of the cortex 260, exteriorly "covered" by the pia 258. With other procedures, the brain tumor 250 may be internal or embedded within the cortex (or other brain tissue) 260. Regardless, once a target site 262 at which the brain tumor 250 is located has been exposed, the system 20 is operated to remove at least some, preferably all, of the brain tumor 250.

The cutting implement 30 is deployed to the target site 262. During delivery of the cutting implement 30, the power supply 26 is inactive, such that the inner member 56 (FIG. 3) does not move relative to the outer member 52. Further, the source of negative pressure 24 may or may not be activated during initial placement of the cutting implement 30. That is to say, a negative pressure condition may or may not be established along the fluid pathway 36. Where the source of negative pressure 24 is activated, however, the user manually effectuates control over delivery of negative pressure to the cutting implement 30, such as by leaving the user interface hole 210 (FIG. 11) associated with the aspiration control device 34 uncovered. As described above, this arrangement causes virtually all of the negative pressure generated by the source of negative pressure 24 to be delivered to the user interface hole 210, and thus not the aspiration outlet/aperture 116 of the cutting implement in a manner that might otherwise negatively impact surrounding tissue of the target site 262.

Figure 12B:
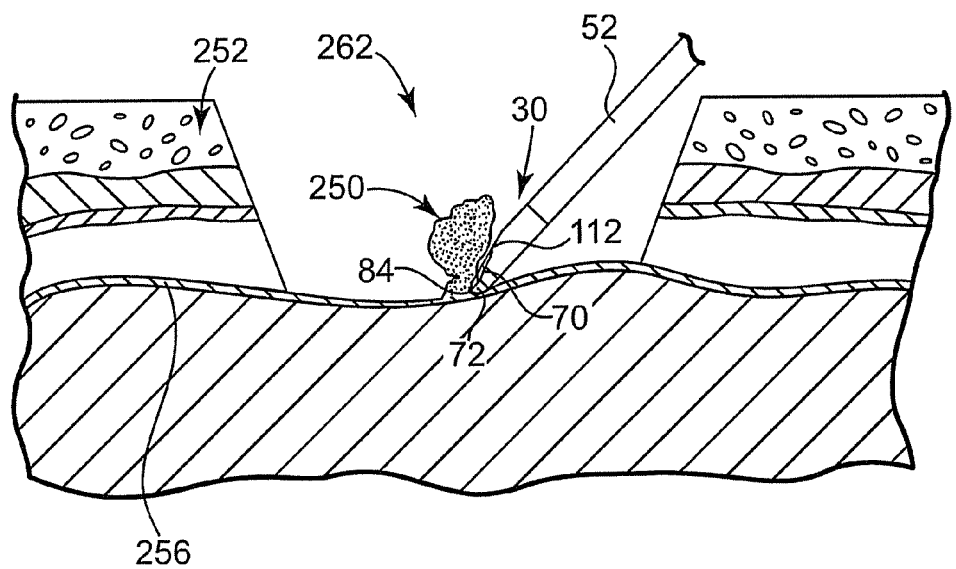

Once the cutting implement 30 is positioned adjacent the brain tumor 250, the surgeon manipulates the handpiece 32 so as to position the elevator tip 72 (where provided) partially between the brain tumor 250 and surrounding tissue of the target site 262. Where provided, the control assembly 40 can be operated by the surgeon to rotate the elevator tip 72 to a desired spatial orientation relative to the target site 262 without overt twisting/contortion of the surgeon's hand(s). For example, as shown in FIG. 12B, the elevator tip 72 is positioned between the brain tumor 250 and a portion of the pia mater 258. Depending upon the particular location of the brain tumor 250, other non-tumor tissue of the brain anatomy may also or alternatively be implicated (e.g., the dura 254, arachnoid 256, cerebral cortex 260, etc.), with the elevator tip 72 partially isolating the brain tumor 250 from this tissue. Regardless, the elevator tip 72 at least partially separates or isolates the brain tumor 250 from the surrounding tissue with the blade edge 84 possibly partially severing a portion of the brain tumor 250 away from the surrounding tissue. For example, the blade edge 84 can be manipulated to pierce the pia 258 at a relatively precise location in close proximity to the tumor 250. Further, by controlling (minimizing) aspiration at the cutting implement, unnecessary damage to the pia 258 (and other tissue) is avoided. The handpiece 32 can be further manipulated to cause the elevator tip 72 to pry the brain tumor 250 away from the surrounding tissue.

Once the elevator tip 72 is desirably positioned, the cutting tip 112 (referenced generally in FIG. 12B) is placed into contact with the brain tumor 250. For example, the outer member 52 is moved (e.g., rotated) such that the cutting window 70 "faces" the brain tumor 250. Further, with some techniques, the aspiration control device 34 is manually operated to effectuate delivery of negative pressure to the cutting implement 30, thus drawing or suctioning the brain tumor 250 into contact with the cutting tip 112. For example, the surgeon can at least partially obstruct the user interface hole 210 (FIG. 11), effectuating a more complete fluid connection between the source of negative pressure 24 and the aspiration aperture 116.

Due to the relatively compact and streamlined size and shape of the handpiece 32, the surgeon can readily, visually confirm desired placement and orientation of the cutting implement 30, and in particular the elevator tip 72 and the cutting window 70/cutting tip 112, relative to the brain tumor 250 and the surrounding tissue. Once the surgeon is satisfied with placement of the cutting implement 30, the power supply 26 is activated, thus causing the inner member 56 (FIG. 3) to move relative to the outer member 52. This action, in turn, causes the cutting tip 112 to move within the cutting window 70, cutting or debriding the contacted brain tumor 250. With some constructions, the motor 132 (FIG. 8) operates to rotationally oscillate the cutting tip 112 relative to the cutting window 70. As part of this debriding procedure, the aspiration control device 34 can be manually operated (e.g., movement of the surgeon's finger relative to the hole 210) to effectuate an increased vacuum level at the cutting implement 30, thus removing debrided brain tumor tissue from the target site 262.

During the debriding procedure, the surgeon can periodically confirm continued desired positioning of the cutting implement 30 relative to the brain tumor 250 and the surrounding tissue 256. Where, for example, it is determined that a differing point of cutting along the brain tumor 250 is desired, the outer member 52 can be rotated relative to the inner member 56 (FIG. 3), thereby altering a spatial position of the cutting window 70, and thus a point of contact of the cutting tip 112 with the brain tumor 250. For example, the actuator 170 (FIG. 8) can be manipulated by the user's finger, causing a rotational position of the outer member 52 relative to the inner member 56 to change. Once again, and throughout the entire procedure, the level of vacuum or rate of aspiration can be manually changed at any time by the surgeon, for example by simply covering more or less of the hole 210 (FIG. 11).

The surgical systems and methods of the present disclosure provide a marked improvement over previous brain tumor surgical techniques. The cutting implement, including the cutting tip and optional elevator tip, can safely remove selected brain tumor tissue, but not damage the surrounding tissues. Further, with selective variable aspiration, the brain tumor tissue can be isolated from the surrounding tissue for subsequent removal and more aggressive cutting. Further, the ability to rotate the outer member assists in protecting the delicate brain anatomy tissue (e.g., dura, arachnoid, pia, etc.).

Although the present disclosure has been described with reference to preferred embodiments, workers skilled in the art will recognize that changes can be made in form and detail without departing from the spirit and scope of the present disclosure.

What is claimed is:

1. A surgical method for treating a brain tumor of a patient, the method comprising:
    providing a surgical system including a source of negative pressure, tubing and a surgical instrument comprising:
        an inner member including a distal cutting tip,
        an outer member having a distal region forming a cutting window and an elevator tip distal the cutting window, wherein the inner member is rotatably received within the outer member such that the cutting tip is exteriorly exposed at the cutting window, the cutting tip and the distal region combining to define a cutting implement, wherein the source of negative pressure is fluidly connected to the cutting implement along a fluid pathway,
        an aspiration control device fluidly connected to the fluid pathway and forming a user interface hole,
        a handpiece defining a first end maintaining the inner member and the outer member and a second end opposite the first end and maintaining an aspiration control port, the inner member coupled to an inner member hub positioned within the handpiece and spaced apart from the second end at a first distance along the fluid pathway, wherein the tubing fluidly connects the source of negative pressure with the aspiration control port, the user interface hole positioned proximate the first end of the handpiece and spaced apart from the second end at a second distance that is greater than or equal to the first distance,
    creating an opening through a skull of the patient to provide external access to a target site at which the brain tumor is located;
    delivering the cutting implement through the opening and to the target site;
    inserting the elevator tip partially between the tumor and tissue of the target site selected from the group consisting of dura, arachnoid, pia, and cerebral cortex;
    placing the cutting tip into contact with the tumor;
    using a motor to move the inner member relative to the outer member to cause the cutting tip to cut tissue of the tumor;
    selectively aspirating the target site to remove the cut tumor tissue.

2. The method of claim 1, wherein selectively aspirating the target site includes:
    manually effectuating an altering of a level of vacuum applied by the source of negative pressure at the cutting implement.

3. The method of claim 2, wherein manually effectuating an altering of a level of vacuum includes changing a position of a user's finger relative to the aspiration control device.

4. The method of claim 3, wherein changing a position of the user's finger is characterized by a hand of the user, otherwise including the finger, holding the handpiece.

5. The method of claim 4, wherein the aspiration control device includes a tube assembled to the handpiece and fluidly connected to the tubing, the tube forming the user interface hole, and further wherein manually effectuating altering of a level of vacuum includes:
    covering more of the user interface hole with the user's finger to increase a level of vacuum applied at the cutting implement; and
    covering less of the user interface hole with the user's finger to decrease a level of vacuum applied at the cutting implement.

6. The method of claim 2, wherein the steps of delivering the cutting implement and inserting the elevator tip between the tumor and tissue of the target site are characterized by:
    the source of negative pressure continuously operating to generate negative pressure; and
    the user manually effectuating a minimization of delivery of the negative pressure to the cutting implement.

7. The method of claim 6, wherein the steps of delivering the cutting implement and inserting the elevator tip are further characterized by tissue of the target site not being suctioned into contact with the cutting tip.

8. The method of claim 2, wherein placing the cutting tip into contact with a tumor includes the user manually effectuating an increase in a level of vacuum applied by the source of negative pressure at the cutting implement to draw the tumor into contact with the cutting tip.

9. The method of claim 8, wherein the inner member is tubular, defining a lumen, and the cutting tip forms an aspiration aperture fluidly open to the lumen, and further wherein the source of negative pressure is fluidly connected to the lumen such that the vacuum is applied at the aspiration aperture.

10. The method of claim 8, wherein placing the cutting tip into contact with the tumor further includes:

visually confirming positioning of the cutting tip relative to tissue of the target site prior to manually effectuating an increase in the level of vacuum applied at the cutting implement.

11. The method of claim 1, wherein the elevator tip forms a blade edge, and further wherein inserting the elevator tip partially between the tumor and tissue of the target site includes:
prying the tumor away from tissue of the target site with the blade edge.

12. The method of claim 1, further comprising:
rotating the elevator tip relative to the cutting tip to change a spatial location of the cutting window relative to the target site prior to moving the inner member relative to the outer member.

13. The method of claim 12, wherein the surgical instrument further includes a handpiece maintaining the inner and outer members, and an actuator adapted to cause the outer member to rotate relative to the inner member, and further wherein rotating the elevator tip includes a user grasping the handpiece in a hand of the user and manipulating the actuator with a finger of the hand.

14. The method of claim 1, wherein moving the inner member to cause the cutting tip to cut tissue of the tumor includes oscillating the inner member relative to the outer member.

15. The method of claim 1, wherein the user interface hole is larger than the cutting window.

16. The method of claim 13, wherein the actuator is positioned between the tube and the handpiece.

17. The method of claim 1, wherein the shape of the tube defines one or more bends.

18. A surgical method for treating a brain tumor of a patient, the method comprising:
providing a surgical system including a source of negative pressure, tubing and a surgical instrument comprising:
an inner member including a distal cutting tip,
an outer member having a distal region forming a cutting window,
wherein the inner member is rotatably received within the outer member such that the cutting tip is exteriorly exposed at the cutting window, the cutting tip and the distal region combining to define a cutting implement, wherein the source of negative pressure is fluidly connected to the cutting implement along a fluid pathway,
an aspiration control device fluidly connected to the fluid pathway and forming a user interface hole,
a handpiece defining a first end maintaining the inner member and the outer member and a second end opposite the first end and maintaining an aspiration control port, the inner member coupled to an inner member hub positioned within the handpiece and spaced apart from the second end at a first distance along the fluid pathway, wherein the tubing fluidly connects the source of negative pressure with the aspiration control port, the user interface hole positioned proximate the first end of the handpiece and spaced apart from the second end at a second distance that is greater than or equal to the first distance,
creating an opening through a skull of the patient to provide external access to a target site at which the brain tumor is located;
delivering the cutting implement through the opening and to the target site;
inserting the cutting window partially between the tumor and tissue of the target site selected from the group consisting of dura, arachnoid, pia, and cerebral cortex;
placing the cutting tip into contact with the tumor;
using a motor to move the inner member relative to the outer member to cause the cutting tip to cut tissue of the tumor;
selectively aspirating the target site to remove the cut tumor tissue.

* * * * *